United States Patent

Sato et al.

[11] Patent Number: 5,599,838
[45] Date of Patent: Feb. 4, 1997

[54] PROSTAGLANDIN DERIVATIVES

[75] Inventors: Fumie Sato, 3-1-219, Kugenuma Higashi, Fujisawa-shi, Japan; Takehiro Amano, Tokyo; Kazuya Kameo, Tokyo; Tohru Tanami, Tokyo; Masaru Mutoh, Tokyo; Naoya Ono, Tokyo; Jun Goto, Tokyo, all of Japan

[73] Assignees: Taisho Pharmaceutical Co., Ltd.; Fumie Sato, both of Japan

[21] Appl. No.: 606,440

[22] Filed: Feb. 23, 1996

[51] Int. Cl.$^6$ ................................................. A61K 31/21
[52] U.S. Cl. ..................... 514/530; 514/573; 560/121; 562/503
[58] Field of Search ................ 560/121; 562/503; 514/530, 573

[56] References Cited

U.S. PATENT DOCUMENTS 4,029,681   6/1977   Smith et al. .................... 560/121

FOREIGN PATENT DOCUMENTS

| | | | |
|---|---|---|---|
| 7242622 | 9/1995 | Japan | 560/121 |
| 7233143 | 9/1995 | Japan | 560/121 |
| 8900559 | 1/1989 | WIPO | 560/121 |
| 9402457 | 3/1994 | WIPO | 560/121 |
| 9518101 | 6/1995 | WIPO | 560/121 |

*Primary Examiner*—James H. Reamer
*Attorney, Agent, or Firm*—Lorusso & Loud

[57] ABSTRACT

A prostaglandin derivative represented by the formula:

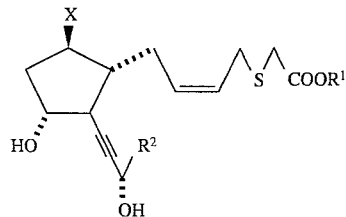

wherein X is halogen atom $R^1$ is a hydrogen atom or an alkyl group having 1 to 6 carbon atoms, and $R^2$ is a cycloalkyl group having 3 to 10 carbon atoms, a cycloalkylmethyl group having 4 to 10 carbon atoms or a cycloalkylethyl group having 5 to 12 carbon atoms, or a salt thereof, which has an excellent lowering action of intraocular pressure and improving actions of renal diseases, ischemic heart diseases and heart failure.

5 Claims, 1 Drawing Sheet

(*p<0.5,**p<0.01)

(*p<0.5)

PROSTAGLANDIN DERIVATIVES

BACKGROUND OF THE INVENTION

1. Field of the Invention

The present invention relates to novel prostaglandin (hereinafter referred to as PG) derivatives, and more particularly relates to novel PG derivatives having an excellent lowering action of intraocular pressure and improving actions of renal diseases, ischemic heart diseases and heart failure, and their use as medicines.

2. Prior Art

Since PGs and derivatives thereof exhibit various important physiological actions in a trace amount, investigations have been made of the synthesis and biological activity of natural PGs and a large number of PG derivatives with the intention of use as medicines. Results of these investigations are reported in many publications, for example, Japanese Patent Kokai No. 52-100446, WO 89/00559 and WO 94/02457. The physiological actions of PGs and derivatives thereof include a vasodilating action, an anti-inflammatory action, an inhibiting action of blood platelet aggregation, a uterine muscle contraction action, an intestinal contraction action and a lowering action of intraocular pressure.

As a result of various researches, the present inventors have found novel PG derivatives having a potent lowering action of intraocular pressure with no or less side effects such as transient ocular hypertension, lacrimation, lid closure or iridal hyperemia, as compared with the prior art compounds, as well as potent improving actions of renal diseases, ischemic heart diseases and heart failure, and thereby the present invention has been accomplished.

SUMMARY OF THE INVENTION

An object of the present invention is to provide a PG derivative represented by Formula (I):

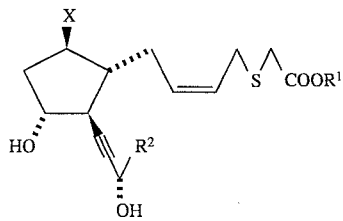

wherein X is halogen atom, $R^1$ is a hydrogen atom or an alkyl group having 1 to 6 carbon atoms, and $R^2$ is a cycloalkyl group having 3 to 10 carbon atoms, a cycloalkylmethyl group having 4 to 11 carbon atoms or a cycloalkylethyl group having 5 to 12 carbon atoms, or a salt thereof.

A further object of the present invention is to provide a pharmaceutical composition comprising a PG derivative of Formula (I) or a salt thereof.

A still further object of the present invention is to provide a method for lowering intraocular pressure of patients comprising administering an effective amount of a PG derivative of Formula (I) or a salt thereof to eyes of patients.

In the specification of the present invention, the alkyl group having 1 to 6 carbon atoms refers to a straight or branched alkyl group such as, for example, a methyl group, an ethyl group, a propyl group, an isopropyl group, an n-butyl group, an isobutyl group or a tert-butyl group. Examples of the cycloalkyl group, or the cycloalkyl moiety of the cycloalkylmethyl group or the cycloalkylethyl group are a cyclopentyl group, a cyclohexyl group and a cycloheptyl group. The halogen atom refers to a fluorine atom, a chlorine atom or a bromine atom. The salt of the compound of Formula (I) refers to a pharmaceutically acceptable salt thereof such as, for example, alkali metal salts (e.g. sodium salt or potassium salt), alkali earth metal salts (e.g. calcium salt or magnesium salt), ammonium salt, tetraalkylammonium salts or salts with amines (e.g. methylamine, dimethylamine, cyclopentylamine, benzylamine, piperidine, monoethanolamine, diethanolamine, monomethylmonoethanolamine, tromethamine or lysine).

Preferred compounds of the present invention are those of Formula (I) wherein $R^1$ is a hydrogen atom or an alkyl group having 1 to 4 carbon atoms, and $R^2$ is a cycloalkyl group having 5 to 7 carbon atoms, and salts thereof. More preferred compounds of the present invention are those of Formula (I) wherein $R^1$ is a hydrogen atom or an alkyl group having 1 to 4 carbon atoms, and $R^2$ is a cyclohexyl group, and salts thereof.

DETAILED DESCRIPTION OF THE INVENTION

Figure 1:
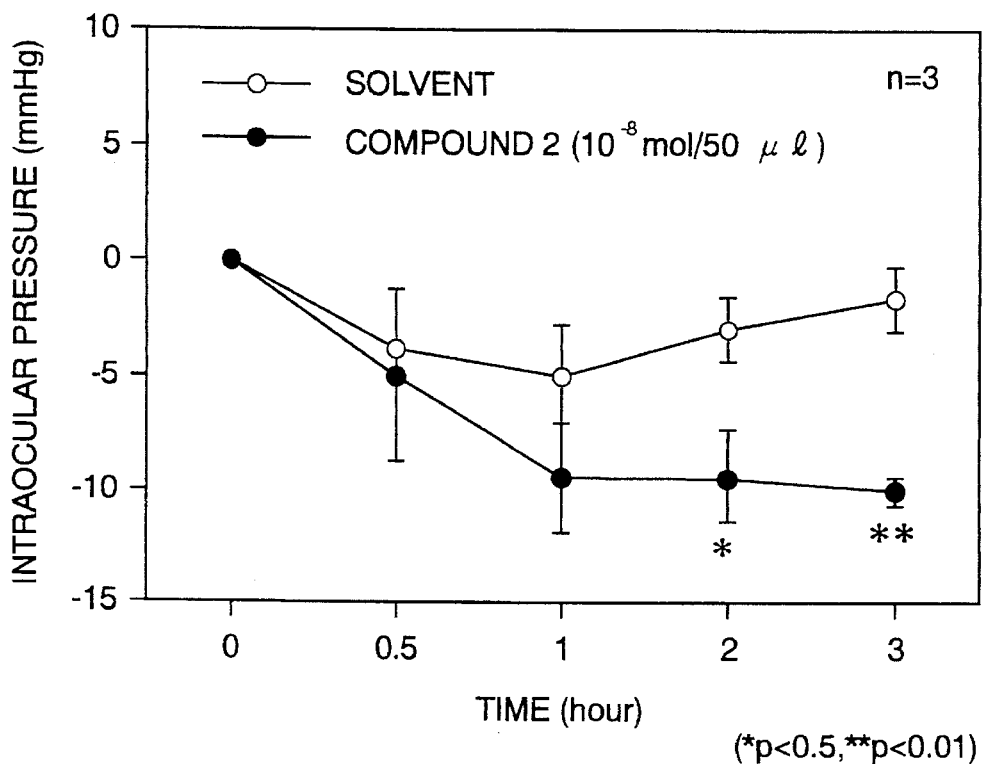
FIG. 1 shows the change with time in the intraocular pressure values of rabbits to which the compounds obtained in the following Example 2 ($10^{-8}$ mol/50 μl) was administered.

The compound of Formula (I) can be prepared, for example, by the following processes.

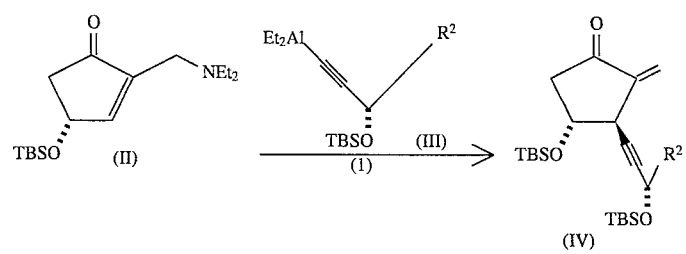

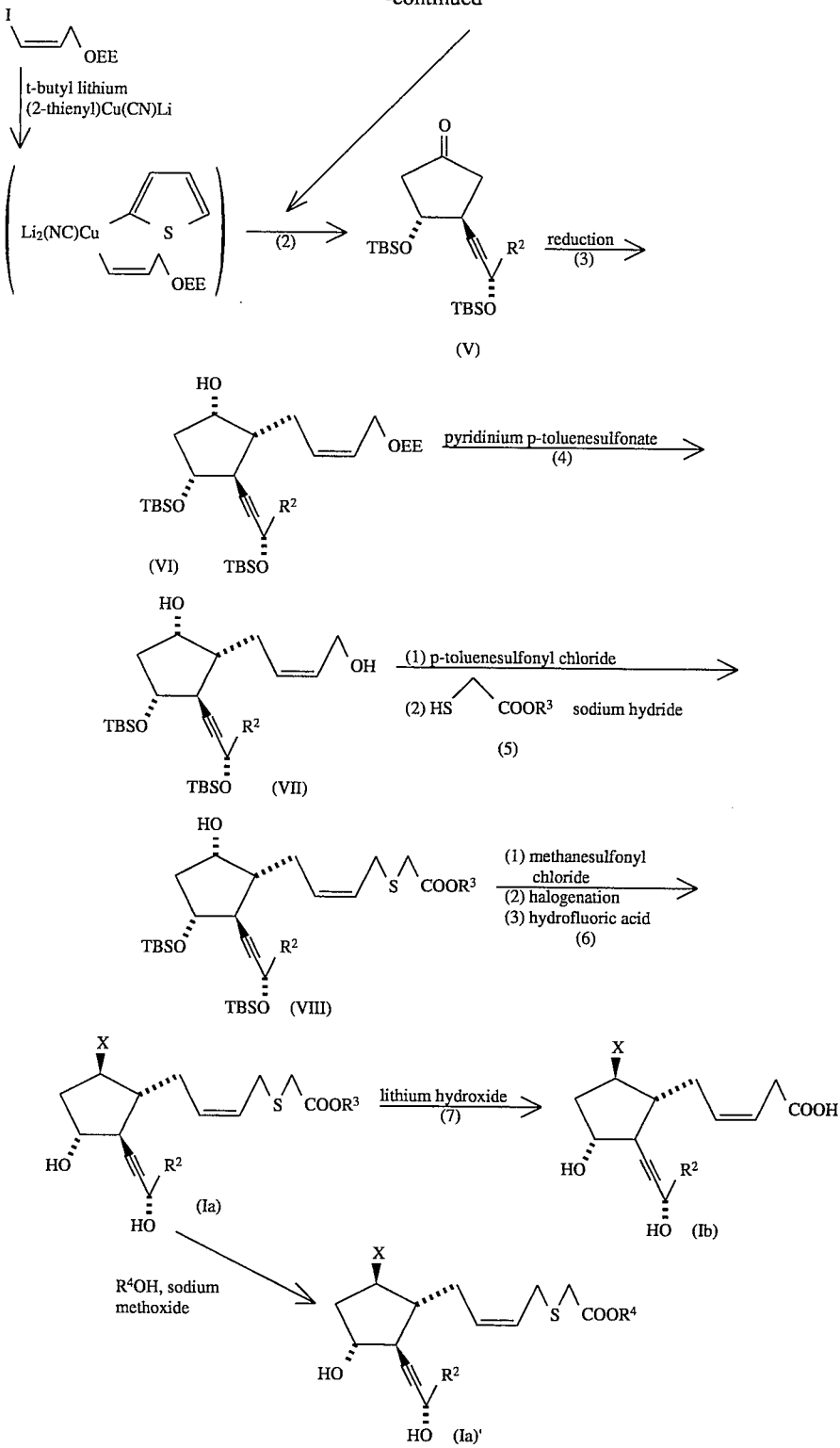

In the above schemes, TBS is a t-butyldimethylsilyl group, Et is an ethyl group, X and $R^2$ are as defined in Formula (I), EE is an ethoxyethyl group, and $R^3$ is the alkyl group defined for $R^1$ in Formula (I), and $R^4$ is the alkyl group as defined for $R^1$ in Formula (I), but not the same as selected for $R^3$.

That is, a compound of Formula (II) is reacted with a compound of Formula (III) to introduce the ω-side chain of PG, thereby giving a compound of Formula (IV). On the other hand, (Z)-1-iodo-3-(1-ethoxyethoxy)-1-propene is reacted with t-butyllithium and a 2-thienylcyanocuprate and then, the resulting compound is reacted with the compound of Formula (IV) to introduce the α-side chain of PG, thereby giving a compound of Formula (V). This compound is stereoselectively reduced with lithium tri-sec-butylborohydride to give a compound of Formula (VI), of which ethoxyethyl group is then deprotected to give a compound of Formula (VII). The primary hydroxyl group of the compound of Formula (VII) is tosylated with p-toluenesulfonyl chloride, and the resulting compound is reacted with a mercaptoacetate using sodium hydride to give a compound of Formula (VIII). Subsequently, the hydroxyl group of the Formula (VIII) is mesylated with methanesulfonyl chloride and then reacted with tetra-n-butylammonium chloride to give a chloro-substituted compound, of which protective group of the hydroxyl group is then removed with hydrofluoric acid to give a compound of Formula (Ia). In the above process, a bromo- or fluoro-substituted compound prepared by bromination or fluorination under ordinary conditions can be used in place of the chloro-substituted compound. For example, the bromination can be carried out by a reaction with carbon tetrabromide in acetonitrile in the presence of triphenylphosphine or pyridine, and the fluorination can be carried out by a reaction with dimethylaminosulfate fluoride (DAST) in methylene chloride. The compound of Formula (Ia) is hydrolyzed with lithium hydroxide to give a compound of Formula (Ib), i.e. a compound of Formula (I) wherein $R^1$ is a hydrogen atom. The compound of Formula (Ia) can be also converted to any other desired ester compounds of Formula (Ia)' by treating with appropriate alcohols in the presence of sodium methoxide.

The compounds of the present invention have a potent lowering action of intraocular pressure with no or little side effects, and therefore can be useful for the treatment of glaucoma and other diseases caused by increased intraocular pressure.

Furthermore, the compounds of the present invention possess higher selectivity in renal vasodilatory and coronary vasodilatory actions than in systemic peripheral vasodilatory action, with long duration of the actions. It is also considered that the compounds of the present invention would potentiate the renal function because the compounds showed an excellent acceleration of glomerular filtration and an excellent diuretic action. Accordingly, these compounds are also useful for the treatment of renal diseases, ischemic heart diseases and heart failure.

For these purposes, the compounds of the present invention are administered orally or parenterally such as intravenously, by instillation or rectally. The compounds of the present invention can be used with a pharmaceutically acceptable carrier. For oral administration, the compounds may be used in the form of solid preparations such as, for example, tablets, granules or capsules, in the form of liquid preparations such as, for example, solutions, fat emulsions or liposome suspensions. For intravenous administration, the compounds of the present invention can be used in the form of aqueous or non-aqueous solutions, emulsions or suspensions, or in the form of solid preparations to be dissolved in a solvent for injection immediately before use. Furthermore, the compounds can be used in the form of suppositories for rectal administration, or in the form of pessaries for intravaginal administration.

For ophthalmic administration, the compounds of the present invention can be used in the form of ophthalmic preparations such as sterile aqueous solutions, aqueous suspensions, non-aqueous solutions, non-aqueous suspensions or ointments. In this case, the compounds of the present invention may be contained in the amount of 0.0001 to 0.01% by weight. A diluent to be used for the aqueous solutions or suspensions includes distilled water or physiological saline. A diluent to be used for the non-aqueous solutions or suspensions includes vegetable oils, liquid paraffin, mineral oils, propylene glycol or p-octyldodecanol. Also contained in the preparations may be components such as isotonic agents for making the same osmotic pressure as that of tears (e.g. sodium chloride or potassium chloride), buffer solutions (e.g. borate buffer, phosphate buffer, citrate buffer or carbonate buffer), stabilizers (e.g. sodium sulfite or EDTA), thickening agents (e.g. glycerin or carboxymethyl cellulose), preservatives (e.g. parabens, chlorobutanol, benzalkonium chloride or sorbic acid), solubilizers (polysorbate 80, polyoxyethylene hardened caster oil or propylene glycol), pH regulators, conventional choline-type ocular hypotensive agents, miotic agents (e.g. pilocarpine), hyperostotic agents (e.g. mannitol), antiseptic agents (e.g. chlorobutanol) or preventional or therapeutical agents of inflammation (e.g. penicillin or sulfonamide). These components can be contained after asepsis by sterilization filtration.

For ophthalmic ointments, bases (e.g. vaseline, selen 50, plastibase or maclogols), surfactants (e.g. polysorbate or purified lanoline), jellies (e.g. carboxymethyl cellulose, methylcellulose or carboxyvinyl polymer) can be also contained.

The compounds of the present invention can be formulated into the form of the inclusion compounds with α–, β– or γ-cyclodextrin, or methylated cyclodextrin.

The dose of the compounds of the present invention can be appropriately decided after consideration of the conditions, body weight, age, sex of the patient. In general, the daily dose for adults is from 0.05 to 60 µg for intravenous administration or for rectal administration, from 1 to 600 µg for oral administration, and from 0.0001 to 10 µg/eye for ophthalmic administration, and it is given in single or several divided doses.

Experiment 1 [Lowering Activity of Rabbit Intraocular Pressure]

White rabbit intraocular pressure was determined by according to the method of Goh et al (British Journal of Ophthalmology, vol. 72, page 461, 1988). White rabbits, weighing 2.0 to 2.5 kg, were fixed in holders for oral administration, and corneal surface anesthetization was provided by instillation of one or two drops of a xylocaine solution (Fujisawa Pharmaceutical Co.) for ophthalmology. Subsequently, intraocular pressure was measured by using an electrotonometer (Alcon Inc.) from the gas pressure given by a sensor connected to a silicone rubber plate attached to rabbit cornea. The measurement was repeated 3 times at intervals of 15 minutes, and the medium value of the intraocular pressures of both eyes serves as a control.

The compound of the present invention dissolved in a solvent (a physiological saline containing 10% ethanol) ($10^{-8}$, $10^{-10}$ mol/50 µl) was topically administered to the left eye of each rabbit, and 50 µl of the solvent only was similarly administered to the right eye. After the administration, intraocular pressure was measured at 0.5, 1, 2 and 3 hours. The compound of the present invention used herein is that of Formula (I) wherein $R^1$ is an isopropyl group, $R^2$ is a cyclohexyl group and X is a β-chlorine atom (Compound 2).

Statistical analysis was conducted by comparison of the intraocular pressure value before administration and the intraocular pressure values at the designated times after the administration according to paired T-test. Significant level is 5% of two-sided risk rate, and p<5% represents a significant difference. Three rabbits were used for each group.

Figure 2:
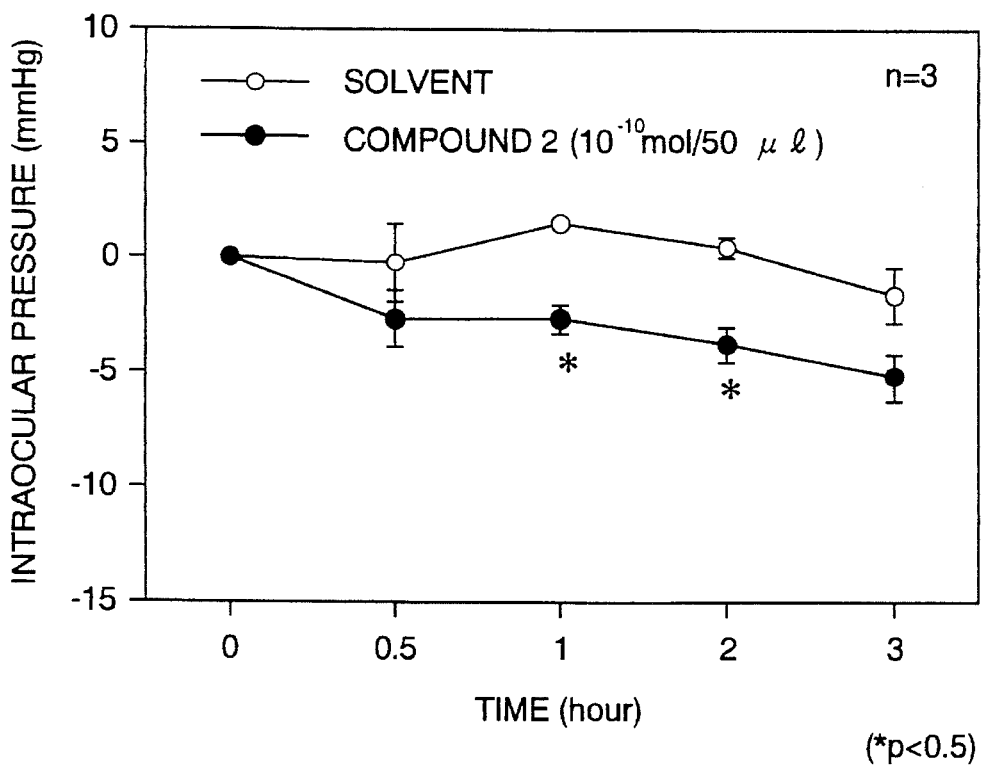
FIG. 2 shows the change with time in the intraocular pressure values of rabbits to which the compounds obtained in the following Example 2 ($10^{-10}$ mol/50 μl) was administered.

The change with time in the intraocular pressure values of rabbits to which the ophthalmic solutions of the compounds in the desired concentrations ($10^{-8}$, $10^{-10}$ mol/50 μl) were administered are shown in FIGS. 1 and 2.

By the administration of the ophthalmic solution containing the compound of the present invention, intraocular pressure was promptly lowered without observation of any side-effects. Furthermore, elevation of intraocular pressure prior to the lowering of intraocular pressure was not observed in the groups administered in any concentrations. On the other hand, there was observed no significant change in eyes to which the solvent was administered, and side effects were not observed after the administration.

Experiment 2 [Renal Vasodilator Activity and Hypotensive Activity]

Mongrel dogs of both sexes weighing 7 to 11 kg, 4 dogs for each group, were anesthetized with sodium pentobarbital (30 mg/kg, i.v.). The blood pressure was measured by using a pressure transducer (TP-400T, Nippon Koden) connected to a catheter inserted backwardly into the femoral artery, through an amplifier for strain pressure (AP-630G, Nippon Koden). The heart rate was measured by recording the arterial wave as a trigger pulse by using a heart rate counter (AT-600G, Nippon Koden). The left abdomen was incised, a probe for electromagnetic flowmeter connected to an electromagnetic flowmeter (MFV-2100, Nippon Koden) was fixed in the left renal artery, and the renal blood flow was measured at the peak of the reaction induced by the administration of the test drug according to the method of Tsuchida et al. described in Arzneim. Forsch., vol. 36, p. 1745 (1986). Each drug was dissolved in ethanol; $PGE_1$, Control Drug A and the compound of the invention obtained in Example 1 (Compound 1) were intravenously administered through the femoral vein in doses of 300 to 3000 pmol/kg, 10 to 3000 pmol/kg and 1 to 300 pmol/kg, respectively. Each dose was 1 μl/kg. The renal blood flow increasing activity or hypotensive activity of each drug was evaluated by the dose causing 15% increase in the renal blood flow or by the dose causing 5% fall in the blood pressure, in terms of activity ratio when the activity of Control drug A was regarded as 1.

TABLE 1

| Test drug | Activity ratio | |
|---|---|---|
| | Renal blood Flow increasing activity | Hypotensive activity |
| $PGE_1$ | 0 | 2.0 |
| Control drug A | 1.0 | 1.0 |
| Compound 2 | 4.0 | 6.6 |

NOTE
Control drug A:

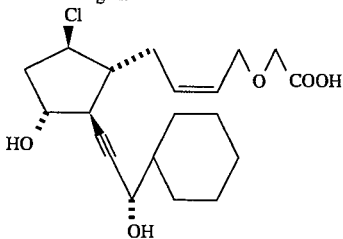

BEST MODE FOR CARRYING OUT THE INVENTION

The present invention is illustrated in more detail by the following examples.

EXAMPLE 1

Preparation of 3-thia-9-deoxy-9β-chloro-13,14-didehydro-16,17,18,19,20-pentanor-15-cyclohexVl-$PGF_2$

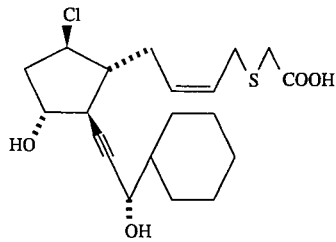

(1) To a solution of (3S)-3-t-butyldimethylsiloxy-3-cyclohexylprop-1-yne (3.61 g) in benzene (28.8 ml) was added n-butyl lithium (1.95M, hexane solution, 6.4 ml) at 0° C., followed by stirring at the same temperature for 30 minutes. Diethylaluminium chloride (0.97M, hexane solution, 14.8 ml) was added to the solution at 0° C. and warmed to room temperature and then stirred for 30 minutes. (4R)-2-(N,N-diethylamino)methyl-4-(t-butyldimethylsiloxy)cyclopent-2-en-1-one (0.25M, hexane solution, 38.4 ml) was added to the solution at room temperature, followed by stirring for 15 minutes.

The reaction solution was poured into a mixture of hexane (100 ml)—a saturated aqueous ammonium chloride solution (100 ml)—an aqueous hydrochloric acid solution (3M, 30 ml) with stirring, and the organic layer was separated and washed with a saturated aqueous sodium bicarbonate solution (50 ml). The resulting organic layer was dried and concentrated, and the resulting residue was purified by silica gel column chromatography (eluent; hexane:ether=10:1) to give 3.69 g of (3R, 4R)-2-methylene-3-[(3'S)-3'-(t-butyldimethylsiloxy)-3'-cyclohexylprop-1'-ynyl]-4-(t-butyldimethylsiloxy)cyclopentan-1-one, of which analytical values are shown as follows:

$^1$H-NMR (CDCl$_3$, 300 MHz) δppm:
0.07, 0.08 and 0.12 (3s, 12H), 0.88 (s, 18H), 0.92-1.92 (m, 11H), 2.32 (dd, J=17.8 Hz, 7.4 Hz, 1H), 2.71 (dd, J=17.8 Hz, 6.5 Hz, 1H), 3.48-3.58 (m, 1H), 4.11 (dd, J=6.2 Hz, 1.4 Hz, 1H), 4.20-4.32 (m, 1H), 5.55 (d, J=2.6 Hz, 1H), 6.13 (d, J=3.0 Hz, 1H)

IR (neat):
2930, 2850, 1735, 1640, 1470, 1380, 1255, 1105, 830, 770 cm$^{-1}$ (2) To an ether solution (12.8 ml) of (Z)-1-iodo-3-(1-ethoxyethoxy)-1-propene (1.72 g, 6.42 mmol) was added dropwise a pentane solution (7.55 ml, 1.7M, 12.84 mmol) of t-butyl lithium at −78° C. followed by stirring for 40 minutes, and a tetrahydrofuran solution (33.4 ml, 0.25M, 8.35 mmol) of (2-thienyl)Cu(CN)Li was added thereto. The mixture was stirred at −78° C. for 10 minutes, after which an ether solution (20 ml) of the compound obtained in the item (1) (2.04 g, 4.28 mmol) was added dropwise thereto. After heating to room temperature with stirring over a period of about an hour, the reaction solution was poured into a mixture of hexane (100 ml) and a saturated aqueous ammonium chloride solution (100 ml) with stirring. The organic layer was separated, and the aqueous layer was extracted with hexane (50 ml). The resulting organic layer was dried over anhydrous magnesium sulfate and filtered. The filtrate was concentrated under reduced pressure, and the resulting crude product was purified by silica gel column chromatography (eluent; hexane:ether=6:1) to give 2.17 g of 2-decarboxy-2,3,16,17,18,19,20-heptanor-4-(1-ethoxyethoxy)-15-cyclohexyl-13,14-didehydro-PGE$_2$11,15-bis(t-butyldimethylsilyl)ether, of which analytical values are shown as follows:

$^1$H-NMR (CDCl$_3$, 300 MHz) δppm:
0.07, 0.09, 0.10 and 0.12 (4s, 12H), 0.89 (s, 18H), 1.20 (t, J=7.0 Hz, 3H), 1.31 (d, J=4.7 Hz, 3H), 0.93-1.91 (m, 11H), 2.14 (dd, J=18.3 Hz, 7.3 Hz, 1H), 2.20-2.36 (m, 1H), 2.40-2.58 (m, 2H), 2.60-2.77 (m, 2H), 3.42-3.70 (m, 2H), 4.02-4.21 (m, 3H), 4.23-4.32 (m, 1H), 4.71 (q, J=4.7 Hz, 1H), 5.48-5.72 (m, 2H)

(3) A tetrahydrofuran solution (20 ml) of the compound obtained in the item (2) (1.42 g, 2.29 mmol) was cooled to −78° C., and L-Selectride (2.97 ml, 1M tetrahydrofuran solution, 2.97 mmol) was added dropwise thereto. After stirring at −78° C. for an hour, the mixture was heated to room temperature over a period of about an hour. To the mixture was added dropwise 35% aqueous hydrogen peroxide solution (3 ml), followed by stirring at room temperature for 15 minutes, and then a saturated aqueous ammonium chloride solution (50 ml) and ether (50 ml) were added thereto. The organic layer was separated, and the aqueous layer was extracted with ether (30 ml). The resulting organic layer was dried over anhydrous magnesium sulfate and filtered. The filtrate was concentrated under reduced pressure, and the resulting crude product was purified by silica gel column chromatography (eluent; hexane: ether=2:1) to give 870 mg of 2-decarboxy-2,3,16,17,18,19,20-heptanor-4-(1-ethoxyethoxy)-15-cyclohexyl-13,14-didehydro-PGF$_2$α11,15-bis(t-butyldimethylsilyl)ether, of which analytical values are shown as follows:

$^1$H-NMR (CDCl$_3$, 300 MHz) δppm:
0.08 and 0.10 (2s, 12H), 0.88 and 0.89 (2s, 18H), 1.00-1.50 (m, 6H), 1.21 (t, J=7.1 Hz, 3H), 1.32 (d, J=5.3 Hz, 3H), 1.50-1.92 (m, 7H), 2.00-2.60 (m, 4H), 3.01 (t, J=7.8 Hz, 1H), 3.40-3.73 (m, 2H), 3.92-4.30 (m, 5H), 4.65-4.82 (m, 1H), 5.50-5,73 (m, 2H)

(4) To a solution of the compound obtained in the item (3) (727 mg, 1.19 mmol) in a mixture of i-PrOH (6 ml) and ether (6 ml) was added pyridinium p-toluenesulfonate (15 mg, 0.06 mmol), followed by stirring at room temperature for 10 hours. To the mixture was added successively ether (20 ml) and a saturated aqueous sodium bicarbonate solution (30 ml), and the organic layer was separated. The aqueous layer was extracted with ether (2×10 ml), and the resulting organic layer was dried over anhydrous magnesium sulfate and filtered. The filtrate was concentrated under reduced pressure, and the resulting crude product was purified by silica gel column chromatography to give 550 mg of 2-decarboxy-2,3,16,17,18,19,20-heptanor-4-hydroxy-15-cyclohexyl-13,14-didehydro-PGF$_2$α 11,15-bis(t-butyldimethylsilyl)ether, of which analytical values are shown as follows:

$^1$H-NMR (CDCl$_3$, 300 MHz) δppm:
0.08, 0.09, 0.10 and 0.11 (4s, 12H), 0.89 and 0.90 (2s, 18H), 0.93-1.32 (m, 5H), 1.38-1.52 (m, 1H), 1.61-1.93 (m, 7H), 1.95-2.07 (m, 1H), 2.20-2.30 (m, 1H), 2.41-2.75 (m, 4H), 3.88 (dd, J=12.0 Hz, 6.2 Hz, 1H), 4.04-4.13 (m, 2H), 4.26-4.33 (m, 1H), 4.38 (dd, J=12.0 Hz, 8.8 Hz, 1H), 5.59 (dt, J=5.0 Hz, 10.8 Hz, 1H), 5.77-5.88 (m, 1H)

$^{13}$C-NMR (CDCl$_3$, 75 MHz) δppm:
132.2, 129.3, 85.5, 83.7, 80.5, 83.7, 73.9, 67.9, 57.4, 53.1, 45.0, 44.9, 42.8, 28.7, 27.0, 26.5, 26.0, 25.8, 18.3, 17.9, −4.43, −4.77, −4.99

$[α]_D^{36.0}$ −5.00° (C=1.786, chloroform)

(5) To a methylene chloride solution (1.6 ml) of the compound obtained in the item (4) (553.1 mg, 0.997 mmol) and diisopropylethylamine (1.6 ml) was added p-toluenesulfonyl chloride (931 mg, 4.89 mmol) under ice-cooling with stirring, followed by stirring at room temperature for 20 hours. After addition of a saturated aqueous sodium bicarbonate solution, the mixture was extracted with hexane, and the resulting organic layer was dried over anhydrous magnesium sulfate. The mixture was filtered, and the resulting filtrate was concentrated under reduced pressure and purified by silica gel column chromatography (eluent; hexane:ether= 5:1) to give 2-decarboxy-2,3,16,17,18,19,20-heptanor-4-chloro-15-cyclohexyl-13,14-didehydro-PGF$_2$ α11,15-bis(t-butyldimethylsilyl)ether (480.6 mg).

To a THF solution (4.0 ml) of sodium hydride (137.6 mg, 2.58 mmol) was added methyl mercaptoacetate (0.16 ml, 1.72 mmol) under ice-cooling with stirring, followed by stirring at room temperature for 30 minutes. To the solution was added dropwise a THF solution (4.6 ml) of 2-decarboxy-2,3,16,17,18,19,20-heptanor-4-chloro-15-cyclohexyl-13,14-didehydro-PGF$_2$ α11,15-bis(t-butyldimethylsilyl)ether (476.6 mg, 0.86 mmol) obtained above under ice-cooling with stirring, followed by stirring at room temperature for 3 hours. The reaction solution, after addition of a saturated aqueous sodium bicarbonate solution, was extracted with hexane. The resulting organic layer was dried over anhydrous magnesium sulfate and filtered. The resulting filtrate was concentrated under reduced pressure and purified by silica gel column chromatography (eluent; hexane:ether=5:1) to give 3-thia-13,14-didehydro-16,17,18,19, 20-pentanor-15-cyclohexyl-PGF$_2$α methyl ester 11,15-bis(t-butyldimethylsilyl)ether (297 mg), of which analytical values are shown as follows:

$^1$H-NMR (CDCl$_3$, 300 MHz) δppm:
0.07, 0.09, 0.10 and 0.11 (4s, 12H), 0.88 and 0.89 (2s, 18H), 0.93-1.30 (m, 5H), 1.38-1.52 (m, 1H), 1.61-1.90 (m, 7H), 1.98-2.09 (m, 1H), 2.28-2.99 (m, 2H), 2.50-2.58 (m, 1H), 2.68 (d, J=8.8 Hz, 1H), 3.22 (s, 2H), 3.32 (dd, J=13.1 Hz, 7.6 Hz, 1H), 3.40 (dd, J=13.1 Hz, 8.0 Hz, 1H), 3.73 (s, 3H), 4.04-4.12 (m, 2H), 4.23-4.29 (m, 1H), 5.44-5.74 (m, 2H)

IR (neat):
3500, 2940, 2860, 2225, 1740, 1440, 1225, 1100, 1008, 940, 840, 780 cm$^{-1}$ (6) To a pyridine solution (2.3 ml) of the compound obtained in the item (5) (278 mg, 0.44 mmol) was added methanesulfonyl chloride (0.55 μl, 0.71 mmol) under ice-cooling with stirring and after heating to room temperature, the mixture was stirred for 5 hours. The reaction solution was added dropwise to a toluene solution (2.3 ml) of tetrabutylammonium chloride (2.0 g) with stirring at room temperature, and the mixture was heated to 50° C., followed by stirring for a further 4 hours. The reaction solution was poured into ice water and extracted with ether. The extract was washed with a saturated aqueous sodium chloride solution, dried over anhydrous magnesium sulfate and filtered. The filtrate was concentrated under reduced pressure, and the resulting crude product was purified by silica gel column chromatography (eluent; hexane: ethyl acetate=1) to give 246.5 mg of 3-thia-9-deoxy-9β-chloro-13,14-didehydro-16,17,18,19,20-pentanor-15-cyclohexyl-PGF$_2$ methyl ester 11,15-bis(t-butyldimethylsilyl)ether, of which analytical values are shown as follows:

$^1$H-NMR (CDCl$_3$, 300 MHz) δppm: 0.07 (s, 3H), 0.08 (s, 6H), 0.11 (s, 3H), 0.75-1.90 (m, 12H), 0.88 (s, 9H), 0.90 (s, 9H), 2.07-2.21 (m, 2H), 2.28-2.48 (m, 2H), 2.34 (ddd, J=9.5 Hz, 5.1 Hz, 1.5 Hz, 1H), 3.21 (s, 2H), 3.23-3.44 (m, 2H), 3.74 (s, 3H), 3.89-4.05 (m, 1H), 4.08 (dd, J=6.2 Hz, 1.6 Hz, 1H), 4.19-4.30 (m, 1H), 5.48-5.78 (m, 2H)

IR (neat):
2953, 2929, 2856, 2234, 1741, 1472, 1463, 1437, 1389, 1362, 1339, 1278, 1256, 1129, 1101, 1072, 1007, 899, 838, 778, 670 cm$^{-1}$ (7) To a THF solution (10 ml) of the compound obtained in the item (6) (227.4 mg, 0.353 mmol) was added a mixture of an aqueous hydrofluoric acid solution (3.2 ml) and THF (3.5 ml) under ice-cooling with stirring, and the mixture was stirred for 4 hours while heating to room temperature. The reaction solution was poured into a mixture of ethyl acetate (30 ml) and a saturated aqueous sodium bicarbonate solution (30 ml) with stirring, the organic layer was separated, and the aqueous layer was extracted with ethyl acetate (20 ml). The resulting organic layer was dried over anhydrous magnesium sulfate and then filtered. The filtrate was concentrated under reduced pressure, and the resulting crude product was purified by silica gel column chromatography (eluent; ethyl acetate:methanol=50:1) to give 154.8 mg of 3-thia-9-deoxy-9β-chloro-13,14-didehydro-16,17,18,19,20-pentanor-15-cyclohexyl-PGF$_2$ methyl ester, of which analytical values are shown as follows:

$^1$H-NMR (CDCl$_3$, 300 MHz) δppm:
0.82-1.44 (m, 5H), 1.45-1.98 (m, 6H), 2.08-2.61 (m, 8H), 3.17 (s, 2H), 3.23-3.40 (m, 2H), 3.70 (s, 3H), 3.80-4.52 (m, 3H), 5.32-5.84 (m, 2H)

IR (neat):
3400, 2925, 2860, 2670, 2240, 1725, 1440, 1278, 1135, 1010, 890 cm$^{-1}$ (8) To a methanol (4.0 ml)—water (0.22 ml) solution of the compound obtained in the item (7) (87.5 mg, 10.21 mmol) was added lithium hydroxide monohydrate (44.1 mg, 1.05 mmol), followed by stirring at room temperature for 4 hours. The mixture, after addition of ethyl acetate (18 ml), was adjusted to pH 6.5 by gradually adding 0.1N aqueous hydrochloric acid solution, and then ammonium sulfate (5 g) was added thereto. The mixture was extracted with ethyl acetate (2×18 ml), and the resulting organic layer was dried over anhydrous magnesium sulfate and filtered. The filtrate was concentrated under reduced pressure, and the resulting crude product was purified by silica gel column chromatography (eluent; ethyl acetate:methanol=3:1) to give 61.3 mg of the title compound, of which analytical values are shown as follows:

$^1$H-NMR (CDCl$_3$, 300 MHz) δppm:
0.98-1.35 (m, 5H), 1.45-1.52 (m, 1H), 1.63-1.92 (m, 5H), 2.02-2.60 (m, 9H), 3.15-3.23 (m, 2H), 3.24-3.34 (m, 1H), 3.41-3.50 (m, 1H), 3.98-4.07 (m, 1H), 4.20-4.29 (m, 1H), 4.30-4.39 (m, 1H), 5.51-5.80 (m, 2H)

$^{13}$C-NMR (CDCl$_3$, 75 MHz) δppm:
174.4, 129.7, 127.2, 85.8, 82.7, 76.0, 67.3, 58.5, 54.7, 44.1, 43.6, 32.4, 28.9, 28.7, 28.4, 28.3, 26.4, 25.8

$[\alpha]_D^{36.0}$ −3.51° (C=0.672 chloroform)

EXAMPLE 2

Preparation of 3-thia-9-deoxy-9β-chloro-13,14-didehydro-16,17,18,19,20-pentanor-15-cyclohexyl-PGF$_2$ isopropyl ester

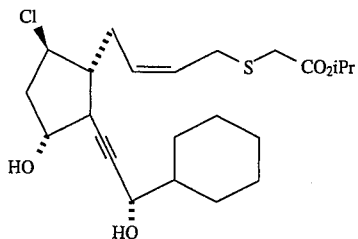

To an i-PrOH (10 ml) solution of the compound obtained in Example 1 (7) (96 mg, 0.23 mmol) was added sodium methoxide (5 mg, 0.093 mmol), followed by stirring at room temperature for 10 minutes. After addition of diethyl ether (20 ml), the mixture was washed with a saturated aqueous ammonium chloride solution (20 ml) and a saturated aqueous sodium chloride solution (20 ml) and dried over anhydrous magnesium sulfate. After filtration, the filtrate was concentrated under reduced pressure, and the resulting crude product was purified by silica gel column chromatography (eluent; hexane: ethyl acetate=2:1) to give 84 mg of the title compound.

$^1$H-NMR (CDCl$_3$, 300 MHz) δppm:
0.96-1.35 (m, 5H), 1.27 (d, J=6.3 Hz, 6H), 1.46-1.91 (m, 8H), 2.14-2.49 (m, 5H), 2.38 (ddd, J=10.2 Hz, 6.3 Hz, 1.9 Hz, 1H), 3.16 (s, 3H), 3.27-3.46 (m, 2H), 3.95-4.05 (m, 1H), 4.16 (dd, J=6.0 Hz, 1.8 Hz, 1H), 4.32-4.40 (m, 1H), 4.97-5.11 (m, 1H), 5.55-5.74 (m, 2H)

IR (neat):
3401, 2981, 2928, 2854, 2237, 1727, 1451, 1387, 1376, 1288, 1146, 1105, 1011, 966, 894, 776, 691 cm$^{-1}$

What is claimed:

1. A prostaglandin derivative represented by the formula:

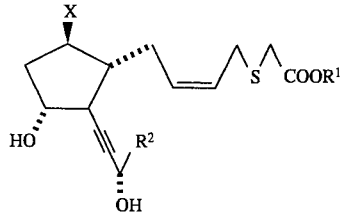

wherein X is halogen atom, R$^1$ is a hydrogen atom or an alkyl group having 1 to 6 carbon atoms, and R$^2$ is a cycloalkyl group having 3 to 10 carbon atoms, a cycloalkylmethyl group having 4 to 10 carbon atoms or a cycloalkylethyl group having 5 to 12 carbon atoms, or a salt thereof.

2. The prostaglandin derivative of claim 1 wherein R$^1$ is a hydrogen atom or an alkyl group having 1 to 4 carbon atoms, and R$^2$ is a cycloalkyl group having 5 to 7 carbon atoms or a salt thereof.

3. The prostaglandin derivative of claim 1 wherein R$^1$ is a hydrogen atom or an alkyl group having 1 to 4 carbon atoms, and R$^2$ is a cyclohexyl group or a salt thereof.

4. A pharmaceutical composition comprising the prostaglandin derivative of claim 1 or a salt thereof.

5. A method for lowering intraocular pressure in patients comprising administering an effective amount of the prostaglandin derivative of claim 1 or a salt thereof to eyes of patients.

* * * * *

UNITED STATES PATENT AND TRADEMARK OFFICE
CERTIFICATE OF CORRECTION

PATENT NO. : 5,599,838
DATED : February 4, 1997
INVENTOR(S) : SATO et al

It is certified that error appears in the above-indentified patent and that said Letters Patent is hereby corrected as shown below:

Col. 2, line 25, "diethanoiamine" should read --diethanoamine--.

Col. 5, line 37, "withlong" should read --with long--.

Col. 7, line 40, before "Table 1" insert --Results are shown in Table 1--.

Col. 8, line 6, "cyclohexVl" should read --cyclohexyl--.

Col. 9, line 67, "C=1.786" should read --c=1.786--.

Col. 10, line 59, "acetate=1" should read --acetate=4:1--.

Col. 11, line 57, "C=0.672" should read --c=0.672--.

Signed and Sealed this

Twenty-third Day of December, 1997

Attest:

BRUCE LEHMAN

Attesting Officer

Commissioner of Patents and Trademarks